United States Patent [19]

Dutzmann et al.

[11] Patent Number: 4,845,117
[45] Date of Patent: Jul. 4, 1989

[54] COMBATING PSEUDOCERCOSPORELLA HERPOTRICHOIDES 1-(4-CHLOROPHENYL)-4,4-DIMETHYL-3-(1,2,4-TRIAZOL-1-YL-METHYL)-PENTAN-3-OL

[75] Inventors: Stefan Dutzmann, Duesseldorf; Paul Reinecke; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 204,463

[22] Filed: Jun. 9, 1988

[30] Foreign Application Priority Data

Jun. 25, 1987 [DE] Fed. Rep. of Germany ....... 3720998

[51] Int. Cl.⁴ .............................. A01N 00/00
[52] U.S. Cl. ................................. 514/383
[58] Field of Search ........................ 514/383

[56] References Cited

U.S. PATENT DOCUMENTS 4,675,316 6/1987 Chaw ................................. 514/383
4,723,984 2/1988 Holmwood et al. ............... 514/383

FOREIGN PATENT DOCUMENTS 0052424 5/1982 European Pat. Off. .

*Primary Examiner*—Allen J. Robinson
*Attorney, Agent, or Firm*—Sprung, Horn, Kramer & Woods

[57] ABSTRACT

The known compound 1-(4-chlorophenyl)-4,4-dimethyl-3-(1,2,4-triazol-1-yl-methyl)-pentan-3-ol of the formula

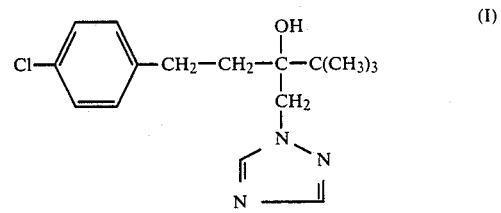

in particularly suitable for combating Pseudocercosporella herpotrichoides.

2 Claims, No Drawings

COMBATING PSEUDOCERCOSPORELLA HERPOTRICHOIDES 1-(4-CHLOROPHENYL)-4,4-DIMETHYL-3-(1,2,4-TRIAZOL-1-YL-METHYL)-PENTAN-3-OL

The invention relates to the use of the known compound 1-(4-chlorophenyl)-4,4-dimethyl-3-(1,2,4-triazol-1-yl-methyl)-pentan-3-ol for combating Pseudocercosporella herpotrichoides.

It is already known that 1-(4-chlorophenyl)-4,4-dimethyl-3-(1,2,4-triazol-1-yl-methyl)-pentan-3-ol has a very good fungicidal activity (compare European Published Specification No. 0,040,345). However, specific use of this substance against Pseudocercosporella herpotrichoides has not yet been described.

It has now been found that 1-(4-chlorophenyl)4,4-dimethyl-3-(1,2,4-triazol-1-yl-methyl)-pentan-3-ol of the formula $$Cl-C_6H_4-CH_2-CH_2-\underset{\underset{N \diagdown N}{\overset{CH_2}{|}}}{\overset{\overset{OH}{|}}{C}}-C(CH_3)_3 \quad (I)$$

is particularly suitable for use for combating Pseudocercosporella herpotrichoides.

Surprisingly, 1-(4-chlorophenyl)-4,4-dimethyl-3-(1,2,4-triazol-1-yl-methyl)-pentan-3-ol of the formula (I) exhibits a considerably better activity when used against Pseudocercosporella herpotrichoides than the already known substances of the same type of action which have a very similar structure.

The active compound which can be used according to the invention and is defined unambiguously by formula (I) is already known (compare European Published Specification No. 0,040,345).

The substance which can be used according to the invention is outstandingly suitable for combating Pseudocercosporella herpotrichoides, the causative organism of stem break disease in cereals. The substance which can be used according to the invention is preferably used in combating Pseudocercosporella herpotrichoides in wheat and barley.

The active compound can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or the use forms prepared therefrom by further dilution, such as ready-to-use solutions, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The use of the active compound according to the invention can be seen from the following example, which also shows its activity relative to closely related compounds:

EXAMPLE A

Pseudocercosporella herpotrichoides test (wheat)/protective Solvent: 100 parts by weight of dimethylformamide Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew moist. After the spray coating has dried on, the plants are inoculated at the stem base with spores of Pseudocercosporella herpotrichoides.

The plants are placed in a greenhouse at a temperature of about 10° C. and a relative atmospheric humidity of about 80%.

Evaluation is carried out 21 days after the inoculation.

The active compounds, active compound concentrations and test results can be seen from the following table.

TABLE A

Pseudocercosporella herpotrichoides test (wheat)/protective

| Active compound | Active Compound concentration in the spray liquor in % by weight | Disease infestation in % of the untreated control |
|---|---|---|
| Comparison Compounds | | |
| (A) Ph-CH$_2$-CH$_2$-C(OH)(C(CH$_3$)$_3$)-CH$_2$-(1,2,4-triazol-1-yl) | 0.025 | 62.5 |
| (B) 4-F-C$_6$H$_4$-CH$_2$-CH$_2$-C(OH)(C(CH$_3$)$_3$)-CH$_2$-(1,2,4-triazol-1-yl) | 0.025 | 75.0 |
| (C) 2,4-Cl$_2$-C$_6$H$_3$-OCH$_2$-C(OH)(C(CH$_3$)$_3$)-CH$_2$-(1,2,4-triazol-1-yl) | 0.025 | 75.0 |
| (D) 4-F-C$_6$H$_4$-OCH$_2$-C(OH)(C(CH$_3$)$_3$)-CH$_2$-(1,2,4-triazol-1-yl) | 0.025 | 90.9 |

TABLE A-continued
Pseudocercosporella herpotrichoides test (wheat)/protective

| Active compound | Active Compound concentration in the spray liquor in % by weight | Disease infestation in % of the untreated control |
| --- | --- | --- |
| (E) biphenyl-O-CH$_2$-C(OH)(C(CH$_3$)$_3$)-CH$_2$-(1,2,4-triazol-1-yl) | 0.025 | 87.5 |
| (F) 4-chloro-biphenyl-O-CH$_2$-C(OH)(C(CH$_3$)$_3$)-CH$_2$-(1,2,4-triazol-1-yl) | 0.025 | 87.5 |
| according to the invention | | |
| (I) 4-Cl-C$_6$H$_4$-CH$_2$-CH$_2$-C(OH)(C(CH$_3$)$_3$)-CH$_2$-(1,2,4-triazol-1-yl) | 0.025 | 27.3 |

It is understood that the specification and examples are illustrative but not limitative of the present invention and that other embodiments within the spirit and scope of the invention will suggest themselves to those skilled in the art.

We claim:

1. A method of combating Pseudocercosporella herpotrichoides fungus on cereal comprising applying to said fungus a fungicidally effective amount of 1-(4-chlorophenyl)-4,4-dimethyl-3-(1,2,4-triazol-1-yl-methyl)-pentan-3-ol of the formula

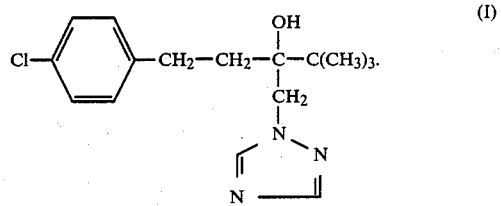

(I)

2. The method according to claim 1, wherein the cereal is wheat.

* * * * *